United States Patent
Fagerhad et al.

(10) Patent No.: US 7,241,923 B2
(45) Date of Patent: Jul. 10, 2007

(54) PHENYLALKYLOXY-PHENYL DERIVATIVES

(75) Inventors: Jonas Fagerhad, Molndal (SE); Lanna Li, Molndal (SE); Lindstedt Alstermark Eva-Lotte, Molndal (SE)

(73) Assignee: Astrazeneca AB, Sodertalje (SE)

( * ) Notice: Subject to any disclaimer, the term of this patent is extended or adjusted under 35 U.S.C. 154(b) by 406 days.

(21) Appl. No.: 10/478,810

(22) PCT Filed: May 30, 2003

(86) PCT No.: PCT/SE02/01039

§ 371 (c)(1),
(2), (4) Date: Nov. 26, 2003

(87) PCT Pub. No.: WO02/096863

PCT Pub. Date: Dec. 5, 2002

(65) Prior Publication Data

US 2004/0176444 A1  Sep. 9, 2004

(30) Foreign Application Priority Data

Jun. 1, 2001 (SE) .................................... 0101978

(51) Int. Cl.
*C07C 275/32* (2006.01)
*A61K 31/17* (2006.01)

(52) U.S. Cl. ............................ 564/53; 564/54; 514/596

(58) Field of Classification Search .................. 564/53, 564/54; 514/596
See application file for complete search history.

(56) References Cited

U.S. PATENT DOCUMENTS 6,699,904 B2 * 3/2004 Hayward et al. ........... 514/535

FOREIGN PATENT DOCUMENTS

| WO | WO-95/17394 A1 | 6/1995 |
| WO | WO-99/19313 A1 | 4/1999 |
| WO | WO-99/62870 A1 | 12/1999 |
| WO | WO-99/62871 A1 | 12/1999 |
| WO | WO-99/62872 A1 | 12/1999 |
| WO | WO-00/50414 A1 | 8/2000 |
| WO | WO-00/63189 A1 | 10/2000 |
| WO | WO-01/40170 A1 | 8/2001 |

OTHER PUBLICATIONS

Brittain "polymorphism in pharmaceutical solids" marcel Dekker, p. 1, 2, 178-179, 185, 219 and 236 (1999).*
A. Maureen Rouhi, Chemical & Engineering News, Feb. 24, 2003, pp. 32-35.*

* cited by examiner

*Primary Examiner*—Rebecca Anderson
(74) *Attorney, Agent, or Firm*—Anita Skeppstedt Pepper Hamilton LLP

(57) ABSTRACT

The present invention relates to certain phenalkyloxy-phenyl derivatives of formula (I) and analogs, to a process for preparing such compounds, having the utility in clinical conditions associated with insulin resistance, to methods for their therapeutic use and to pharmaceutical compositions containing them.

16 Claims, No Drawings

PHENYLALKYLOXY-PHENYL DERIVATIVES

CROSS-REFERENCE TO RELATED APPLICATIONS

This application is a national stage filing under 35 U.S.C. 371 of International Application No. PCT/SE02/01039, filed May 30, 2002, which claims priority from United Kingdom Patent Application No. 0101978.1, filed Jun. 1, 2001, the specification of which is incorporated by reference herein. International Application No. PCT/SE02/01039 was published under PCT Article 21(2) in English

FIELD OF INVENTION

The present invention relates to certain phenalkyloxyphenyl derivatives of formula I and analogs, to a process for preparing such compounds, having the utility in clinical conditions associated with insulin resistance, to methods for their therapeutic use and to pharmaceutical compositions containing them.

BACKGROUND OF THE INVENTION

Insulin resistance, defined as reduced sensitivity to the actions of insulin in the whole body or individual tissues such as skeletal muscle, myocardium, fat and liver prevail in many individuals with or without diabetes mellitus. The insulin resistance syndrome, IRS, refers to a cluster of manifestations including insulin resistance with accompanying hyperinsulinemia, possibly type 2 diabetes mellitus, arterial hypertension, central (visceral) obesity, dyslipidemia observed as deranged lipoprotein levels typically characterised by elevated VLDL (very low density lipoproteins) and reduced HDL (high density lipoproteins) concentrations, the presence of small, dense LDL (Low Density Lipoprotein) particles and reduced fibrinolysis.

Recent epidemiological research has documented that individuals with insulin resistance run a greatly increased risk of cardiovascular morbidity and mortality, notably suffering from myocardial infarction and stroke. In non-insulin dependent diabetes mellitus these atherosclerosis related conditions cause up to 80% of all deaths.

In clinical medicine there is at present only limited awareness of the need to increase the insulin sensitivity in IRS and thus to correct the dyslipidemia which is considered to cause the accelerated progress of atherosclerosis.

Furthermore there is at present no pharmacotherapy available to adequately correct the metabolic disorders associated with IRS. To date, the treatment of type 2 diabetes mellitus has been focused on correction of the deranged control of carbohydrate metabolism associated with the disease. Stimulation of endogenous insulin secretion by means of secretagogues, like sulphonylureas, and if necessary administration of exogenous insulin are methods frequently used to normalise blood sugar but that will, if anything, further enhance insulin resistance and will not correct the other manifestations of IRS nor reduce cardiovascular morbidity and mortality. In addition such treatment involves a significant risk of hypoglycemia with associated complications.

Other therapeutic strategies have focused on aberrations in glucose metabolism or absorption, including biguanides, such as methformin, or glucosidase inhibitors, such as acarbose. Although these agents have been efficacious to a degree, their limited clinical effect is associated with side effects.

A novel therapeutic strategy involves the use of insulin sensitising agents, such as the thiazolidinediones which at least in part mediate their effects via an agonistic action on nuclear receptors. Ciglitazone is the prototype in this class. In animal models of IRS these compounds seem to correct insulin resistance and the associated hypertriglyceridemia and hyperinsulinemia, as well as hyperglycemia in diabetes, by improving insulin sensitivity via an effect on lipid transport and handling, leading to enhanced insulin action in skeletal muscle, liver and adipose tissue.

Ciglitazone as well as later described thiazolidinediones in clinical development either have been discontinued reportedly due to unacceptable toxicity or show inadequate potency.

Therefore there is a need for new and better compounds with insulin sensitising properties.

Co-pending PCT application SE00/02383 discloses the use of compounds of the general formula (I) for the treatment of conditions related to insulin resistance

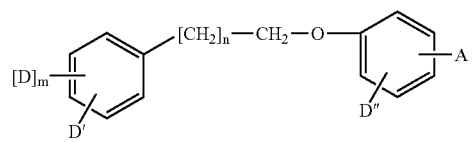

and stereo and optical isomers and racemates thereof as well as pharmaceutically acceptable salts, prodrugs, solvates and crystalline forms thereof, in which formula A is situated in the ortho, meta or para position and represents

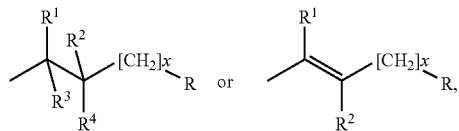

wherein

R is cyano, when X is 0, and when X is 1 then R is;
—$BR^a$ or $SCOR^a$, wherein B is O, S, SO or $SO_2$, wherein $R^a$ represents hydrogen, alkyl, aryl or alkylaryl and wherein the alkyl, aryl or alkylaryl group is optionally substituted one or more times by $R^b$, wherein $R^b$ represents alkyl, aryl, alkylaryl, cyano, —$NR^cR^c$, =O, halogen, —OH, —SH, -Oalkyl, -Oaryl, -Oalkylaryl, —$COR^c$, —$SR^d$, —$SOR^d$, or —$SO_2R^d$, wherein $R^c$ represents hydrogen, alkyl, aryl or alkylaryl and $R^d$ represents alkyl, aryl or alkylaryl;
—$BB^1R^a$, wherein $B^1$ is O when B is S, SO or $SO_2$ or $B^1$ is S, SO or $SO_2$ when B is O, and wherein B and $R^a$ are as defined above, or alternatively R is N $R^a$ $R^a$, wherein each $R^a$ is the same or different and wherein $R^a$ is defined above;
$R^2$ represents alkyl, halogen, aryl, alkylaryl, alkenyl, alkynyl, nitro or cyano and wherein the alkyl, aryl, alkenyl, alkylaryl and alkynyl group is optionally substituted by $R^b$, wherein $R^b$ is as defined above;
—$BR^a$ wherein B and $R^a$ are as defined above;
—$SO_2NR^aR^f$ wherein $R^f$ represents hydrogen, alkyl, acyl, aryl or alkylaryl and $R^a$ is as defined above;

—SO$_2$OR$^a$, wherein R$^a$ is as defined above;
—OCONR$^f$R$^a$, wherein R$^f$ and R$^a$ are as defined above;
—NR$^c$COOR$^d$, wherein R$^c$ and R$^d$ are as defined above;
—NR$^c$COR$^a$, wherein R$^c$ and R$^a$ are as defined above;
—CONR$^c$R$^a$, wherein R$^c$ and R$^a$ are as defined above;
—NR$^c$SO$_2$R$^d$, wherein R$^c$ and R$^d$ are as defined above;
—NR$^c$CONR$^a$R$^k$, wherein R$^a$ and R$^c$ are as defined above and R$^k$ represents hydrogen, alkyl, aryl, or alkylaryl;
alternatively R$^2$ is —NR$^c$R$^a$, wherein R$^c$ and R$^a$ are as defined above;
R$^1$, R$^3$ and R$^4$ are the same or different and each represents hydrogen, alkyl, aryl, alkenyl, alkynyl, cyano, halogen or alkylaryl wherein the alkyl, aryl, alkenyl or alkynyl group is optionally substituted by R$^b$;
n is an integer from 1 to 6;
X is an integer 0 or 1;
m is an integer 0 or 1;
D is situated in the ortho, meta or para position and represents alkyl, acyl, aryl, alkylaryl, halogen, —CN and NO$_2$, wherein the alkyl, aryl, or alkylaryl group is optionally substituted by R$^b$;
—NR$^c$COOR$^a$, wherein R$_c$ and R$^a$ are as defined above;
—NR$^c$COR$^a$, wherein R$^c$ and R$^a$ are as defined above;
—NR$^c$R$^a$, wherein R$^c$ and R$^a$ are as defined above;
—NR$^c$SO$_2$R$^d$, wherein R$^c$ and R$^d$ are as defined above;
—NR$^c$CONR$^k$R$^c$, wherein R$^a$, R$^c$ and R$^k$ are as defined above;
—NR$^c$CSNR$^a$R$^k$, wherein R$^a$, R$^c$ and R$^k$ as defined above;
—OR$^a$, wherein R$^a$ is as defined above;
—OSO$_2$R$^d$, wherein R$^d$ is as defined above;
—SO$_2$R$^d$, wherein R$^d$ is as defined above;
—SOR$^d$, wherein R$^d$ is as defined above;
—SR$^c$, wherein R$^c$ is as defined above;
—SO$_2$NR$^a$R$^f$, wherein R$^f$ and R$^a$ are as defined above;
—SO$_2$OR$^a$, wherein R$^a$ is as defined above;
—CONR$^c$R$^a$, wherein R$^c$ and R$^a$ are as defined above;
—OCONR$^f$R$^a$, wherein R$^f$ and R$^a$ are as defined above;
D' is situated in the ortho, meta or para position and represents hydrogen, alkyl, acyl, aryl, alkylaryl, halogen, —CN, —NO$_2$,
—NR$^f$R$^b$, wherein R$^f$ and R$^b$ are as defined above;
—OR$^f$, wherein R$^f$ is as defined above;
—OSO$_2$R$^d$, wherein R$^d$ is as defined above;
D" is situated in the ortho, meta or para position and represents hydrogen, alkyl, acyl, aryl, alkylaryl, halogen, —CN, —NO$_2$,
—NR$^f$R$^b$ wherein R$^f$ and R$^b$ are as defined above;
—OR$^f$, wherein R$^f$ is as defined above;
—OSO$_2$R$^d$, wherein R$^d$ is as defined above.
Compounds disclosed in this application are disclaimed from the present application.

DESCRIPTION OF THE INVENTION

The invention relates to compounds of the general formula (I)

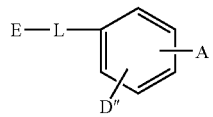

I and stereo and optical isomers and racemates thereof as well as pharmaceutically acceptable salts, prodrugs, solvates and crystalline forms thereof, in which formula A is situated in the ortho, meta or para position and represents

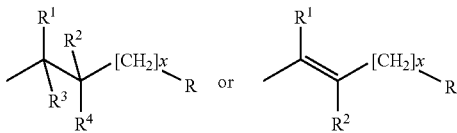

wherein R is cyano, when x is 0, and when x is 1 then R is:
—BR$^a$, OCOR$^a$ or SCOR$^a$, wherein B is O, S, SO or SO$_2$ wherein R$^a$ represents hydrogen, alkyl, aryl, alkylaryloxy or alkylaryl and wherein the alkyl, aryl or alkylaryl group is optionally substituted one or more times by R$^b$, wherein R$^b$ represents alkyl, aryl, alkylaryl, cyano, —NR$^c$R$^c$, =O, halogen, —OH, —SH, -Oalkyl, -Oaryl, -Oalkylaryl, —COR$^c$, —SR$^d$, —SOR$^d$, or —SO$^2$R$^d$ (preferably R$^b$ is selected from alkyl, aryl, alkylaryl, cyano, —NH$_2$, =O, halogen and —OH), wherein R$^c$ represents hydrogen, alkyl, aryl or alkylaryl and R$^d$ represents alkyl, aryl or alkylaryl;
—BB$^1$R$^a$, wherein B$^1$ is O when B is S, SO or SO$_2$ or B$^1$ is S, SO or SO$_2$ when B is O, and wherein B and R$^a$ are as defined above;
or alternatively R is —NR$^a$R$^a$, wherein each R$^a$ is the same or different and wherein R$^a$ is defined above;
R$^2$ represents alkyl, halogen, aryl, alkylaryl, alkenyl, alkynyl, nitro or cyano and wherein the alkyl, aryl, alkenyl, alkylaryl and alkynyl group is optionally substituted by R$^b$, wherein R$^b$ is as defined above;
—BR$^a$ wherein B and R$^a$ are as defined above;
—SO$_2$NR$^a$R$^f$, wherein R$^f$ represents hydrogen, alkyl, acyl, aryl or alkylaryl and R$^a$ is as defined above;
—SO$_2$OR$^a$, wherein R$^a$ is as defined above;
—OCONR$^f$R$^a$, wherein R$^f$ and R$^a$ are as defined above;
—NR$^c$COOR$^d$, wherein R$^c$ and R$^d$ are as defined above;
—NR$^c$COR$^a$, wherein R$^c$ and R$^a$ are as defined above;
—CONR$^c$R$^a$, wherein R$^c$ and R$^a$ are as defined above;
—NR$^c$SO$_2$R$^d$, wherein R$^c$ and R$^d$ are as defined above;
—NR$^c$CONR$^a$R$^k$, wherein R$^a$ and R$^c$ are as defined above and R$^k$ represents hydrogen, alkyl, aryl, or alkylaryl;
alternatively R$^2$ is —NR$^c$R$^a$, wherein R$^c$ and R$^a$ are as defined above;
R$^1$, R$^3$ and R$^4$ are the same or different and each represents hydrogen, alkyl, aryl, alkenyl, alkynyl, cyano, halogen or alkylaryl wherein the alkyl, aryl, alkenyl or alkynyl group is optionally substituted by R$^b$;
x is an integer 0 or 1 (preferably x is 1);
E represents a group of formula i

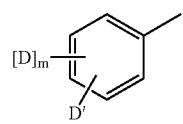

i or a group of formula ii

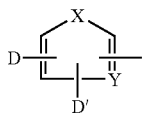

wherein X is S, O, $NR^Z$ wherein $R^Z$ is as defined below, CH=N or N=CH and Y represents CH or N; or X represents —CH=CH— and Y represents N;

or E represents a group of formula iii

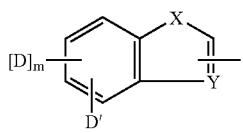

wherein X is S, O, $NR^z$, —CH=N or —N=CH and Y represents CH or N; or X represents —CH=CH— and Y represents N wherein $R^Z$ represents hydrogen, alkyl, aryl, alkyloxyaryl, alkylbiphenylyl, alkoxyalklylaryl, acylbiphenylyl, alkylphthalimido, $SO_2R^Z$, $COR^d$ or alkylaryl (preferably $R^Z$ is selected from hydrogen, alkyl and alkyaryl) and wherein the alkyl, aryl, alkyloxyaryl or alkylaryl group is optionally substituted one or more times by $R^b$, wherein $R^b$ represents alkyl, aryl, alkylaryl, cyano, $—NR^cR^c$, =O, halogen, —OH, —SH, -Oalkyl, -Oaryl, -Oalkylaryl, $—COR^c$, $—SR^d$, $—SOR^d$, or $—SO_2R^d$ (preferably $R^b$ is selected from alkyl, aryl, alkylaryl, cyano, $—NH_2$, =O, halogen and —OH), wherein $R^c$ represents hydrogen, alkyl, aryl or alkylaryl and $R^d$ represents alkyl, aryl or alkylaryl;

or E represents a group of formula iv

C3-C8cycloalkyl     iv or E represents a group of formula v

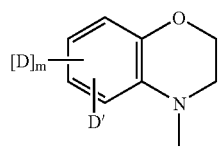

which is linked to L through the nitrogen atom;

or E represents a group of formula vi

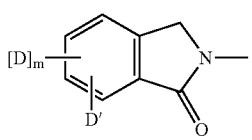

or E represents a group of formula vii

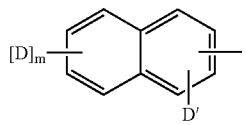

wherein D represents H, alkyl, acyl, aryl, alkylaryl, halogen, —CN and $NO_2$, wherein the alkyl, aryl, or alkylaryl group is optionally substituted by $R^b$;
—$NR^cCOOR^a$, wherein $R^c$ and $R^a$ are as defined above;
—$NR^cCOR^a$, wherein $R^c$ and $R^a$ are as defined above;
—$NR^cR^a$, wherein $R^c$ and $R^a$ are as defined above;
—$NR^cSO_2R^d$, wherein $R^c$ and $R^d$ are as defined above;
—$NR^cCONR^kR^c$, wherein $R^a$, $R^c$ and $R^k$ are as defined above;
—$NR^cCSNR^aR^k$, wherein $R^a$, $R^c$ and $R^k$ are as defined above;
—$OR^a$, wherein $R^a$ is as defined above;
—$OSO_2R^d$, wherein $R^d$ is as defined above;
—$SO_2R^d$, wherein $R^d$ is as defined above;
—$SOR^d$, wherein $R^d$ is as defined above;
—$SR^c$, wherein $R^c$ is as defined above;
—$SO_2NR^aR^f$, wherein $R^f$ and $R^a$ are as defined above;
$SO_2OR^a$, wherein $R^a$ is as defined above;
—$CONR^cR^a$, wherein $R^c$ and $R^a$ are as defined above;
—$OCONR^fR^a$, wherein $R^f$ and $R^a$ are as defined above;
m is an integer 0 or 1 (preferably m is 1);

D' represents hydrogen, alkyl, acyl, aryl, alkylaryl, halogen, —CN, —$NO_2$,
—$NR^fR^b$, wherein $R^f$ and $R^b$ are as defined above;
—$OR^f$, wherein $R^f$ is as defined above;
—$OSO_2R^d$, wherein $R^d$ is as defined above;
CH=CH—$COOR^c$ wherein $R^c$ is as defined above;

D" is represents hydrogen, alkyl, acyl, aryl, alkylaryl, halogen, —CN, —$NO_2$,
—$NR^fR^b$ wherein $R^f$ and $R^b$ are as defined above;
—$OR^f$, wherein $R^f$ is as defined above;
—$OSO_2R^d$, wherein $R^d$ is as defined above;

L represents O or an alkylene chain having from 1 to 6 carbon atoms optionally interrupted or terminated by one or more of the following O, S, SO, $SO_2$, CO, NR', CONR', NR'CO, OC(O)NR', NR'C(O)O, $SO_2NR'$, R'$NSO_2$ or R'N—CO—NR' provided that they are not attached to each other and wherein the alkylene chain carbons may be substituted by one or more alkyl, hydroxy, aryl, aryloxy, arylthio, alkylaryl, cyano, $NR^cR^c$, halo, SH, Oalkylaryl, $COR^c$, —$COR^c$, —$SR^d$, —$SOR^d$, or —$SO_2R^d$, or alkoxy and with the proviso that when E is a group of formula i then L does not represent $[CH_2]_n$—$CH_2$—O in which n is an integer from 1 to 6; and R' represents H, alkyl, aryl, alkylaryl, alkylcycloalkyl, or alkylbiphenylyl wherein each alkyl chain may be substituted by one or more hydroxy or alkoxy and is optionally interrupted by one or more O provided that two hetero atoms are not attached to the same carbon atom.

Preferably L represents O, a C1, C2, C3, C4 or C5 alkylene chain or a group of formula $(CH_2)_aZ^1(CH_2)_bZ^2$ wherein a is 0,1, 2 or 3; $Z^1$ is absent or represents O, S, SO, $SO_2$, CO, NR', CONR', NR'CO, OC(O)NR', NR'C(O)O, $SO_2NR'$, R'$NSO_2$ or R'N—CO—NR', b is 1, 2 or 3 and $Z^2$ is absent or represents O, S, SO, $SO_2$, CO, NR', CONR', NR'CO, OC(O)NR', NR'C(O)O, R'N—CO—NR' wherein R' is as defined above and all of the alkylene chains are optionally substituted by one or more of the following alkyl, hydroxy, aryl, aryloxy, arylthio, alkylaryl, cyano, $NR^cR^c$, halo, SH, Oalkylaryl, $COR^c$, —$COR^c$, —$SR^d$, —$SOR^d$, or —$SO_2R^d$, or alkoxy wherein $R^d$ is as defined above, provided that $Z^1$ and $Z^2$ are not absent simultaneously.

"Pharmaceutically acceptable salt", where such salts are possible, includes both pharmaceutically acceptable acid and base addition salts. A suitable pharmaceutically-acceptable salt of a compound of Formula I is, for example, an acid-addition salt of a compound of Formula I which is sufficiently basic, for example an acid-addition salt with an inorganic or organic acid such as hydrochloric, hydrobromic, sulphuric, trifluoroacetic, citric or maleic acid; or, for example a salt of a compound of Formula I which is sufficiently acidic, for example an alkali or alkaline earth metal salt such as a sodium, calcium or magnesium salt, or an ammonium salt, or a salt with an organic base such as methylamine, dimethylamine, trimethylamine, piperidine, morpholine or tris-(2-hydroxyethyl)amine.

In vivo hydrolysable esters of the compounds of Formula I are just one type of prodrug of the parent molecule. Other prodrugs of the parent molecule are envisaged such as amide prodrugs, and can be prepared by routine methodology well within the capabilities of someone skilled in the art. Prodrugs of the compound of Formula I are within the scope of the invention. Various prodrugs are known in the art. For examples of such prodrug derivatives, see:
a) Design of Prodrugs, edited by H. Bundgaard, (Elsevier, 1985) and Methods in Enzymology. 42: 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8:1–38 (1992);
d) H. Bundgaard, et al., Journal of Pharmaceutical Sciences, 77:285 (1988); and
e) N. Kakeya, et al., Chem Pharm Bull, 32:692 (1984).

The preferred examples of prodrugs include in vivo hydrolysable esters of a compound of the Formula I. Suitable pharmaceutically-acceptable esters for carboxy include $C_{1-8}$alkyl esters, $C_{5-8}$cycloalkyl esters, cyclic amine esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl wherein alkyl, cycloalkyl and cyclicamino groups are optionally substituted by, for example, phenyl, heterocyclcyl, alkyl, amino, alkylamino, dialkylamino, hydroxy, alkoxy, aryloxy or benzyloxy, and may be formed at any carboxy group in the compounds of this invention. Particularly preferred compounds of the present invention are where R represents prodrugs for a hydroxy group.

It will also be understood that certain compounds of the present invention may exist in solvated, for example hydrated, as well as unsolvated forms. It is to be understood that the present invention encompasses all such solvated forms.

When the substituent $OR^a$ represents an alkylaryl group, the preferred alkylaryl is benzyl.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention.

The following definitions shall apply throughout the specification and the appended claims.

Unless otherwise stated or indicated, the term "alkyl" denotes either a straight or branched alkyl group having from 1 to 12 carbon atoms or a cyclic alkyl atom having from 3 to 6 carbon atoms, the alkyl being substituted or unsubstituted. The term "lower alkyl" denotes either a straight or branched alkyl group having from 1 to 3 carbon atoms or a cyclic alkyl having 3 carbon atoms, the alkyl being substituted or unsubstituted. Examples of said alkyl and lower alkyl include methyl, ethyl, n-propyl, isopropyl, n-butyl, iso-butyl, sec-butyl, t-butyl and straight- and branched-chain pentyl and hexyl as well as cyclopropyl, cyclobutyl, cyclopentyl and cyclohexyl. Preferred alkyl groups methyl, ethyl, propyl, isopropyl and tertiary butyl.

Unless otherwise stated or indicated, the term "alkoxy" denotes a group O-alkyl, wherein alkyl is as defined above.

Unless otherwise stated or indicated, the term "halogen" shall mean fluorine, chlorine, bromine or iodine, preferably fluorine.

Unless otherwise stated or indicated, the term "aryl" denotes a substituted or unsubstituted phenyl, furyl, thienyl or pyridyl group, or a fused ring system of any of these groups, such as naphthyl.

Unless otherwise stated or indicated, the term "substituted" denotes an alkyl or an aryl group as defined above which is substituted by one or more alkyl, alkoxy, alkylthio, halogen, amino, thiol, nitro, hydroxy, acyl, aryl or cyano groups.

Unless otherwise stated or indicated, the term "alkylaryl" denotes a

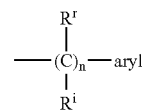

wherein n is an integer 1 to 6 and $R^r$ and $R^i$ are the same or different and each represents hydrogen or an alkyl or aryl group as defined above.

Unless otherwise stated or indicated, the term "acyl" denotes a group

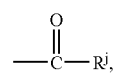

wherein $R^j$ is hydrogen, alkyl, alkoxy, aryl and alkylaryl as defined above.

Unless otherwise stated or indicated, the terms "alkenyl" and "alkynyl" denote a straight or branched, substituted or unsubstituted unsaturated hydrocarbon group having one or more double or triple bonds and having a maximum of 6 carbon atoms, preferably 3 carbon atoms.

Unless otherwise stated or indicated the term "protective group" denotes a protecting group as described in the standard text "Protecting groups in Organic Synthesis", 2nd Edition (1991) by Greene and Wuts. The protective group may also be a polymer resin such as Wang resin or 2-chlorotrityl chloride resin.

Methods of Preparation

The compounds of the invention may be prepared as outlined below according to any of the following methods. However, the invention is not limited to these methods, the compounds may also be prepared as described for structurally related compounds in the prior art.

A. The compounds of Formula I wherein R or $R^2$ is, where defined, $-OR^d$, $-SCOR^d$, $-SR^d$, $-OSO_2R^d$, $-NR^c-COOR^a$, $-NR^cCOR^a$, $-NR^aCONR^aR^k$ or $-NR^cSO_2R^d$ can be prepared by reaction of a compound of Formula I wherein the respective R or $R^2$ group is, for example, $-OH$, $-SH$ or $-NHR^a$ with a suitable reagent, such as a thioate, a sulfonyl halide, an isocyanate, a chloroformate or an addition reagent for ether, such as alkylhalide or arylhalide. The reactions can be carried out in accordance with methods known to those skilled in the art, or as described in the examples. Suitable references are "Comprehensive Organic Transformations" R. C. Larock (VCH Publishers Inc.) 1989, p 445–448, for the formation of alkyl or aryl ethers.

"Advanced Organic Chemistry" J. March (4$^{th}$ edition), John Wiley & Sons, 407–409, for the formation of thioethers, and 498–499, for the formation of sulfonates, 417–418, for the formation of amides, 411–413, for formation of amines.

B. The compounds of Formula I wherein R or $R^2$ is, where defined, $-SR^a$ or $-SCOR^a$ can be prepared by reaction of a compound of Formula I wherein the respective R or $R^2$ group is, for example, $-OSO_2R^a$ with a suitable reagent, respectively. $YSR^a$ or $YSCOR^a$ (wherein Y is a cation). Suitably the reaction is carried out in an inert solvent, such as DMF or methanol at room temprature with a suitable reducing agent, such as sodium borohydride, LiAlH$_4$, or DIBAH.

C. The reduction of the olefin version of the compound of formula I to the saturated version of a compound of formula I may be carried out by using a wide variety of reducing methods known to reduce carbon-carbon double bonds, such as catalytic hydrogenation in the presence of an appropriate catalyst, magnesium or sodium amalgam in a lower alcohol such as-methanol, or hydrogen transfer reagents such as diethyl-2,5-dimethyl-1,4-dihydropyridine-3,5-dicarboxylate.

The catalytic hydrogenation can be conducted in alcohol, cellosolves, protic polar organic solvents, ethers, lower aliphatic acids, and particularly in methanol, ethanol, methoxyethanol, dimethylformamide, tetrahydrofuran, dioxane, dimethoxyethane, ethyl acetate or acetic acid, either used alone or in mixture. Examples of the catalyst used include palladium black, palladium on activated charcoal, platinum oxide or Wilkinson's catalyst. The reaction can proceed at different temperatures and pressures depending on the reactivity of the aimed reaction.

In case of hydrogen transfer reaction with diethyl-2,5-dimethyl-1,4-dihydropyridine-3,5-dicarboxylate, equimolar amounts of reactants are mixed and the mixture is warmed to melting (140° C.–250° C.) under inert atmosphere or under vacuum.

D. The compounds of the invention of formula I can be prepared by an alkylation reaction with a compound of formula VIII

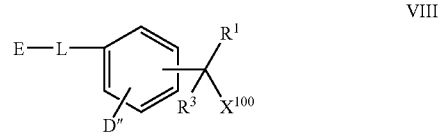

where $X^{100}$ is a leaving group, such as halogen, a sulfonate or triflate, and a compound of formula IXb

in which formulas E, L. $R^1$, $R^2$, $R^3$, $R^4$, $X^{100}$ and D", are as defined above in and, if desired, followed by removal of any protective groups.

In the alkylation step the compound of Formula IX is reacted with a compound of formula VIII in the presence of one or more bases such as potassium carbonate, triethylbenzylammonium chloride, sodium hydride, LDA, butyllithium or LHMDS and in a inert solvent such as acetonitrile, DMF or dichloromethane at a suitable temperature and time. The reaction can be carried out as described in the examples or by standard methods known in the literature (Synth. Comm. 19(788) 1167–1175 (1989)).

The compound of Formula VIII can be prepared from an alcohol of formula X

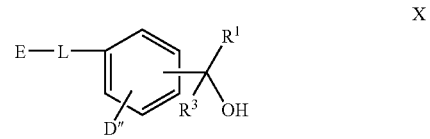

wherein E, L, D" $R^1$, and $R^3$ are as defined above using standard methods.

The compound of Formula X can be prepared from a compound of Formula III either by reduction with a reducing agent known to convert a carbonyl group to a hydroxyl group such as lithium borohydride or sodium borohydride or by reaction with an organometallic compound such as an organolithium or a Grignard reagent by standard methods.

E. The compounds of the invention of Formula I can be prepared by reaction of a compound of formula VI with a compound of the Formula XI

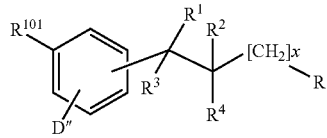

(XI)

in which formulas D", $R^1$, $R^2$, $R^3$, $R^4$, $R^{101}$ x and R are as defined above, in a similar reaction as described above, additional protective groups may be necessary.

The compound of Formula XI can be prepared by known methods from commercially available starting materials and compounds of formula IV or V.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceding methods of preparation A-E, where necessary, hydroxy, amino or other reactive groups may be protected using a protecting group, as described in the standard text "Protective groups in Organic Synthesis", $2^{nd}$ Edition (1991) by Greene and Wuts. The protecting group may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutically acceptable organic or inorganic base addition salt, in a pharmaceutically acceptable dosage form. Depending upon the disorder and patient to be treated and the route of administration, the compositions may be administered at varying doses.

The compounds of the invention may also be combined with other therapeutic agents which are useful in the treatment of disorders associated with the development and progress of atherosclerosis such as hypertension, hyperlipidemias, dyslipidemias, diabetes and obesity.

Suitable daily doses of the compounds of the invention in the therapeutic treatment of humans are about 0.001–10 mg/kg body weight, preferably 0.01–1 mg/kg body weight.

According to a further aspect of the invention there is also provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) are useful for the prophylaxis and/or treatment of clinical conditions associated with reduced sensitivity to insulin (insulin resistance) and associated metabolic disorders. These clinical conditions will include, but will not be limited to, abdominal obesity, arterial hypertension, hyperinsulinaemia, hyperglycaemia, type 2 diabetes mellitus and the dyslipidaemia characteristically appearing with insulin resistance. This dyslipidaemia, also known as the atherogenic lipoprotein profile, phenotype B, is characterised by moderately elevated non-esterified fatty acids, elevated very low density lipoproteins (VLDL) triglyceride rich particles, low high density lipoproteins (HDL) particle levels cholesterol and the presence of small, dense, low density lipoprotein (LDL) particles. Treatment with the present compounds is expected to lower the cardiovascular morbidity and mortality associated with atherosclerosis. These cardiovascular disease conditions include macro-angiophaties causing myocardial infarction, cerebrovascular disease and peripheral arterial insufficiency of the lower extremities. Because of their insulin sensitizing effect the compounds of formula I are also expected to prevent or delay the development of type 2 diabetes and thus reduce the progress of clinical conditions associated with chronic hyperglycaemia in diabetes type 1 such as the micro-angiophaties causing renal disease, retinal damage and peripheral vascular disease of the lower limbs. Furthermore the compounds may be useful in treatment of various conditions outside the cardiovascular system associated with insulin resistance like polycystic ovarian syndrome.

Working Examples $^1$H NMR and $^{13}$C NMR measurements were performed on a Varan Mercury 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta scale (δ).

Unless otherwise stated, chemical shifts are given in ppm with the solvent as internal standard.

| Abbreviations | |
|---|---|
| IRS | insulin resistance syndrome |
| LDA | lithium diisopropylamide |
| LHMDS | lithium hexamethyldisilylamine |
| DMF | dimethylformamide |
| DEAD | diethyl azodicarboxylate |
| ADDP | azodicarbonyl dipiperidine |
| EDC | 1-(3-dimethylaminopropyl)-3-ethylcarbodiimide |
| DCC | dicyclohexylcarbodiimide |
| HBTU | O-benzotriazol-1-yl-N,N,N',N'-tetramethyluronium hexafluorophosphate |
| TBTU | O-benzotriazol-1-yl-N,N,N',N'-tetramethyluronium tetrafluoroborate |
| PyBop | benzotriazole-1-yl-oxy-tris-pyrolidino-phosphonium hexafluorophosphate |
| TEA | triethylamine |
| DIPEA | diisopropylethylamine |
| TLC | thin layer chromatography |
| THF | tetrahydrofuran |
| HO-Su | N-hydroxy succinimide |
| Pd/C | palladium on charcoal |
| HOBtxH$_2$O | 1-hydroxybenzotriazole-hydrate |
| DIBAH | diisobutylaluminium hydride |
| DMSO | dimethyl sulfoxide |

-continued

| Abbreviations | |
|---|---|
| t | triplet |
| s | singlet |
| d | doublet |
| q | quartet |
| qvint | quintet |
| m | multiplet |
| br | broad |
| bs | broad singlet |
| dm | doublet of multiplet |
| bt | broad triplet |
| dd | doublet of doublet |

EXAMPLE 1

N'-(2,4-difluorophenyl)-N-(2-{4-[(2S)-2-ethoxy-3-hydroxypropyl]phenyl}ethyl)-N-heptylurea (i) Ethyl (2S)-2-ethoxy-3-(4-{[(trifluoromethyl)sulfonyl]oxy}phenyl)propanoate Ethyl (2S)-2-ethoxy-3-(4-hydroxyphenyl)propanoate (11.44 g, 48.01 mmol) was dissolved in 240 ml dichloromethane and cooled to −40° C. TEA (7.29 g, 72.04 mmol) was added and the temperature was decreased to −60° C. Trifluoromethane sulfonic anhydride (8.88 ml, 52.81 mmol) was dissolved in 150 ml cold dichloromethane and slowly added to the reaction mixture during 20 minutes. The reaction mixture was stirred at −60° C. for 1.5 hours. The product was washed with cold 1 M potassium hydrogen sulphate solution, the water phase was washed with dichloromethane, the combined organic phases were washed with saturated sodium hydrogen carbonate solution and brine, dried (sodium sulphate), filtered and solvent was evaporated in vacuo to give 17.94 g of a brown oil, which was purified by chromatography on silica gel using heptane:ethyl acetate 2:1 as eluent to give 17.33 g (yield 97.5%) of pure material.

$^1$H-NMR (400 MHz; CDCl$_3$): 1.13 (t, 3H), 1.20 (t, 3H), 2.96–3.07 (m, 2H), 3.28–3.37 (m, 1H), 3.57–3.67 (m, 1H), 3.98 (dd, 1H), 4.15 (q, 2H), 7.17 (dm, 2H), 7.32 (dm, 2H).

$^{13}$C-NMR (100 MHz; CDCl$_3$): 14.0, 14.9, 38.5, 60.9, 66.3, 79.5, 113.9, 117.1, 120.3, 121.0, 123.5, 131.2, 137.9, 141.8, 148.4, 171.9.

(ii) tert-Butyl (2E)-3-{4-[(2S)-2,3-diethoxy-3-oxopropyl]phenyl}acrylate

Ethyl (2S)-2-ethoxy-3-(4-{[(trifluoromethyl)sulfonyl]oxy}phenyl)propanoate (0.994 g, 2.69 mmol), t-butyl acrylate (0.78 ml, 5.37 mmol) and tri-o-tolylphosphine (0.302 g, 0.99 mmol) was dissolved in dry DMF (6 ml) under argon atmosphere. Palladium acetate (72.4 mg, 0.322 mmol) dissolved in some DMF was added and LiBr (1.2 g, 13.81 mmol) and TEA (dried on potassium hydroxide, 0.543 g, 5.37 mmol) was added using some DMF to rinse it down with (10.74 ml DMF was used in total). The reaction mixture was stirred at 90° C. for 64 hours. After 1 h, more TEA (0.75 ml) was added and after 42 hours more TEA (0.75 ml) was added. Water and ethyl acetate were added, but the phases became black and separation of the phases were impossible, therefor the ethyl acetate phase was decanted off and more ethyl acetate was added. This procedure was repeated several times. The combined ethyl acetate phases were washed with water, dried (sodium sulphate), filtered and solvent was evaporated in vacuo, and the crude product was purified by chromatography on silica gel using dichloromethane:methanol (gradient 0–10% methanol) as eluent to give 0.7 g (yield 75%) of the desired product.

$^1$H-NMR (400 MHz; CDCl$_3$): 1.15 (t, 3H), 1.21 (t, 3H), 1.53 (s, 9H), 2.99–3.04 (m, 2H), 3.30–3.39 (m, 1H), 3.57–3.66 (m, 1H), 4.01 (dd, 1H), 4.16 (q, 2H), 6.33 (d, 1H), 7.25 (dm, 2H), 7.43 (dm, 2H), 7.56 (d, 1H).

$^{13}$C-NMR (100 MHz; CDCl$_3$): 14.1, 15.0, 28.2, 39.1, 60.9, 66.2, 79.8, 80.4, 119.7, 127.8, 129.9, 133.1, 139.4, 143.3, 166.3, 172.2.

(iii) Ethyl (2S)-2-ethoxy-3-[4-(3-{tert-butoxy}-3-oxopropyl)phenyl]propanoate tert-Butyl (2E)-3-{4-[(2S)-2,3-diethoxy-3-oxopropyl]phenyl}acrylate (0.614 g, 1.76 mmol) was hydrogenated for 1.5 hours at atmospheric pressure in ethanol (35 ml) using Pd/C (wet, 5%,) as catalyst. The mixture was filtered on hyflo and solvent was evaporated in vacuo to give 0.447 g (yield 72%) of the desired product.

$^1$H-NMR (500 MHz; CDCl$_3$): 1.13 (t, 3H), 1.19, (t, 3H), 1.39 (s, 9H), 2.49 (t, 2H), 2.85 (t, 2H), 2.93–2.97 (m, 2H), 3.28–3.36 (m, 1H), 3.54–3.61 (m, 1H), 3.94–3.99 (m, 1H), 4.13 (m, 2H), 7.07–7.11 (m, 2H), 7.11–7.15 (m, 2H).

$^{13}$C-NMR (125 MHz; CDCl$_3$): 14.1, 14.9, 27.9, 30.6, 36.9, 38.8, 60.6, 66.0, 80.1, 128.1, 129.3, 134.8, 138.9, 172.1, 172.3. (1 carbon is missing)

(iv) 3-{4-[(2S)-2,3-Diethoxy-3-oxopropyl]phenyl}propanoic acid

Trifluoroacetic acid (2.20 ml, 28.45 mmol) was added to a solution of ethyl (2S)-2-ethoxy-3-[4-(3-{tert-butoxy}-3-oxopropyl)phenyl]propanoate (0.43 g, 1.22 mmol) in dichloromethane (4 ml) and stirred for 3 hours at room temperature. Evaporation of solvent in vacuo gave 0.36 g (yield 101%, contains some remaining TFA) of the desired product.

$^1$H-NMR (500 MHz; CDCl$_3$): 1.15 (t, 3H), 1.22 (t, 3H), 2.72 (t, 2H), 2.95 (t, 2H), 3.02–3.06 (m, 2H), 3.40–3.49 (m, 1H), 3.61–3.70 (m, 1H), 4.12–4.16 (m, 1H), 4.21 (q, 2H), 7.12–7.18 (m, 4H).

$^{13}$C-NMR (125 MHz; CDCl$_3$): 13.7, 14.4, 30.0, 35.5, 38.5, 62.2, 66.9, 80.2, 128.2, 129.5, 134.4, 138.4, 174.3, 180.2.

(v) Ethyl (2S)-3-[4-(2-{[(benzyloxy)carbonyl]amino}ethyl)phenyl]-2-ethoxypropanoate 3-{4-[(2S)-2,3-Diethoxy-3-oxopropyl]phenyl}propanoic acid (0.13 g, 0.44 mmol) and dry TEA (47 mg, 0.46 mmol) were dissolved in dry benzene (1.14 ml) under nitrogen atmosphere and stirred for some minutes. Diphenylphosphoryl azide was added and the mixture was refluxed for 30 minutes. Dry benzylalcohol (57 mg, 0.53 mmol) was added and the mixture was refluxed for 20 hours and then stirred at room temperature for 3.5 hours. More benzylalcohol was added (0.15 ml) and the mixture was refluxed for 19 hours more, thereafter solvent was evaporated in vacuo and the crude product was purified by chromatography on silica gel using heptane:ethyl acetate 3:1 as eluent to give 118 mg (yield 67%) of the desired product.

$^1$H-NMR (400 MHz; CDCl$_3$): 1.16 (t, 3H), 1.21 (t, 3H), 2.79 (t, 2H), 2.98 (dd, 2H), 3.31–3.40 (m, 1H), 3.40–3.48

(m, 2H), 3.56–3.65 (m, 1H), 3.97–4.02 (m, 1H), 4.16 (q, 2H), 5.09 (s, 2H), 7.09 (dm, 2H), 7.17 (dm, 2H), 7.32–7.38 (m, 5H).

$^{13}$C-NMR (75 MHz; CDCl$_3$): 14.1, 15.0, 35.6, 38.8, 42.1, 60.8, 66.1, 66.6, 80.1, 128.0, 128.4, 128.5, 128.6, 129.6, 135.3, 136.5, 136.8, 156.2, 172.4.

(vi) Ethyl (2S)-3-[4-(2-aminoethyl)phenyl]-2-ethoxypropanoate

Ethyl (2S)-3-[4-(2-{[(benzyloxy)carbonyl]amino}ethyl)phenyl]-2-ethoxypropanoate (2.45 g, 6.14 mmol) was hydrogenated for 2.5 hours at atmospheric pressure in ethyl acetate (51 ml) using Pd/C (1 spoon) as catalyst. After filtration on hyflo, the solvent was evaporated in vacuo. The crude product was purified by chromatography on silica gel using THF:methanol (NH$_3$-saturated) (gradient 25:1–1:25) as eluent. The first fractions containing the product was filtered on Millipore filter and combined with the later fractions containing product to give 0.84 g (yield 52%, including a by-product) of the desired product.

$^1$H-NMR (400 MHz; CDCl$_3$): 1.15 (t, 3H), 1.20 (t, 3H), 1.82 (bs, 2NH), 2.69–2.78 (m, 2H), 2.9–3.0 (m, 4H), 3.30–3.41 (m, 1H), 3.54–3.64 (m, 1H), 3.97–4.03 (m, 1H), 4.10–4.20 (m, 2H), 7.07–7.17 (m, 4H).

$^{13}$C-NMR (100 MHz; CDCl$_3$): 14.1, 15.0, 38.8, 39.3, 43.3, 60.7, 66.1, 80.1, 128.7, 129.6, 135.0, 137.8, 172.4.

(vii) Ethyl (2S)-2-ethoxy-3-{4-[2-(heptanoylamino)ethyl]phenyl}propanoate

Ethyl (2S)-3-[4-(2-aminoethyl)phenyl]-2-ethoxypropanoate (320 mg 1.206 mmol) and heptanoic acid (157 mg, 1.206 mmol) were mixed in DCM (10 ml). EDC (243 mg, 1.266 mmol) was added and then DMAP (147 mg, 1.206 mmol) was added. The mixture was stirred at room temperature overnight. It was then washed with 1% hydrochloric acid, water, 1% sodium hydrogencarbonate aqueous solution, water and brine and dried with magnesium sulfate. The solvent was evaporated in vacuum. Chromatography of the residue on a column (ISOLUTE, SI, 2 g/6 ml) using DCM, MeOH/DCM (0.5:99.5) and then MeOH/DCM (1:99) as eluant gave 166 mg desired product, yield 37%.

$^1$H NMR (400 MHz, CDCl$_3$): δ 0.89 (t, J=7 Hz, 3H), 1.18 (t, J=7 Hz, 3H), 1.24 (t, J=7 Hz, 3H), 1.26–1.35 (m, 6H), 1.56–1.64 (m, 2H), 2.12 (t, J=7 Hz, 2H), 2.79 (t, J=7 Hz, 2H), 2.99–3.02 (m, 2H), 3.34–3.41 (m, 1H), 3.51 (q, J=7 Hz, 2H), 3.59–3.66 (m, 1H), 4.02 (dd, J=7, 6 Hz, 1H), 4.19 (q, J=7 Hz, 2H), 5.43 (s, br, 1H), 7.12 (d, J=8 Hz, 2H) and 7.20 (d, J=8 Hz, 2H).

(viii) (2S)-2-Ethoxy-3-{4-[2-(heptylamino)ethyl]phenyl}propan-1-ol hydrochloride Ethyl (2S)-2-ethoxy-3-{4-[2-(heptanoylamino)ethyl]phenyl}propanoate (204 mg, 0.54 mmol) in tetrahydrofuran (5 ml, dry) was cooled in an ice-bath. Borane methylsulfide complexe (2 M in ether, 0.7 ml) was added. The cooling bath was removed after 15 minutes. The reaction mixture was heated to reflux gently for 6 hours and then cooled down to room temperature. Hydrochloric acid (10%, 0.3 ml) was dropped in. The mixture was stirred overnight and then evaporated in vacuum to dry. Chromatography of the residue on a column (ISOLUTE, SI, 2 g/6 ml) using DCM, MeOH (1:99) and then MeOH/DCM (2:98) as eluant gave two products. 51 mg of (2S)-2-Ethoxy-3-{4-[2-(heptylamino)ethyl]phenyl}propan-1-ol hydrochloride was obtained as one of them.

$^1$H NMR (400 MHz, CDCl$_3$): δ 0.84 (t, J=7 Hz, 3H), 1.17 (t, J=7 Hz, 3H), 1.21–1.39 (m, 8H), 1.88–1.96(m, 2H), 2.71 (dd, J=14, 8 Hz, 1H), 2.84 (dd, J=14, 6 Hz, 1H), 2.93–2.97 (m, 2H), 3.12–3.28 (m, 4H), 3.41–3.62 (m, 5H), 7.13 (d, J=8 Hz, 2H), 7.16(d, J=8 Hz, 2H) and 9.71 (s, br, 2H).

(ix) N'-(2,4-difluorophenyl)-N-(2-{4-[(2S)-2-ethoxy-3-hydroxypropyl]phenyl}ethyl)-N-heptylurea (2S)-2-Ethoxy-3-{4-[2-(heptylamino)ethyl]phenyl}propan-1-ol hydrochloride (21 mg, 0.059 mmol) and triethyl amine (0.009 ml, 0.065 mmol) were mixed in DCM. 2,4-Di fluorophenyl isocyanate (9.2 mg, 0.059 mmol) was added. The mixture was stirred overnight. Water was added. The organic phase was washed with brine and dried with magnesium sulfate. The solvent was evaporated in vacuum and an oil mixture was left. Chromatography of the oil mixture on a column (ISOLUTE, SI, 200 mg/1 ml) using DCM and MeOH/DCM (1:99) as eluant gave 17 mg desired product, yield 60%.

$^1$H NMR (400 MHz, CDCl$_3$): δ 0.90 (t, J=7 Hz, 3H), 1.19 (t, J=7 Hz, 3H), 1.27–1.35 (m, 8H), 1.59–1.66 (m, 2H), 1.99 (t, J=6 Hz, 1H), 2.72 (dd, J=14, 8 Hz, 1H), 2.86 (dd, J=14, 6 Hz, 1H), 2.91 (t, J=7 Hz, 2H), 3.24 (t, J=7.7 Hz, 2H), 3.40–3.63 (m, 7H), 6.31 (s, br, 1H), 6.81–6.87 (m, 2H), 7.17 (s, 4H) and 8.01–8.07 (m, 1H).

$^{13}$C NMR (100 MHz, CDCl$_3$): δ 14.0, 15.50, 22.53, 26.94, 28.54, 29.0, 31.71, 34.55, 36.99, 48.16, 49.98, 63.60, 65.17, 80.92, 103.11 (t, $^2J_{CF}$=24 Hz), 110.98 (d, $^2J_{CF}$=25 Hz), 122.42 (d, $^3J_{CF}$=8 Hz), 124.02 (m), 128.79 (2C), 129.72 (2C), 136.50, 136.67, 152.28 (d, $^1J_{CF}$=239 Hz), 153.48 and 157.60 (d, $^1J_{CF}$=233 Hz).

Biological Activity

The biological activity of the compounds of the invention is demonstrable in obese diabetic mice of the Umeå ob/ob strain. Groups of mice receive the test compound by gavage once daily for 7 days. On the last day of the experiment the animals are anesthetized 2 h after dose in a non-fed state and blood is collected from an incised artery. Plasma is analyzed for concentration of glucose, insulin and triglycerides. A group of untreated obese diabetic mice of the same age serve as control. The weight of the mice is measured before and after the experiment and the obtained weight gain is compared to the weight gain of the control animals. The individual values for glucose, insulin and triglyceride levels of the mice from the test group are expressed as the percent range of the corresponding values from the control group.

The desired "therapeutic effect" is calculated as the average percent reduction of the three variables glucose, insulin and triglycerides below the levels in the control animals.

The invention claimed is:
1. A compound of formula I

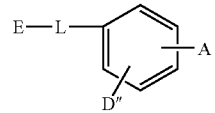

or a stereo isomer, optical isomer, or racemate thereof, or a pharmaceutically acceptable salt, prodrug, or solvate, thereof; wherein:

A is situated in the ortho, meta or para position and represents

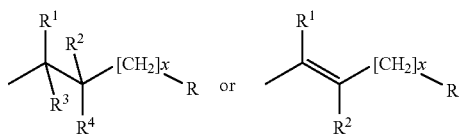

wherein
x is 1;
R is —BR$^a$;
B is O;
R$^a$ represents hydrogen or alkyl, wherein the alkyl group is optionally substituted one or more times by R$^b$; wherein R$^b$ represents alkyl, aryl, alkylaryl, cyano, —NR$^c$R$^c$, =O, halogen, —OH, —SH, —Oalkyl, —Oaryl, —Oalkylaryl, —COR$^c$, —SR$^d$, —SOR$^d$, or —SO$_2$R$^d$; wherein R$^c$ represents hydrogen, alkyl, aryl or alkylaryl; and wherein R$^d$ represents alkyl, aryl or alkylaryl;
R$^2$ is —BR , wherein B and R$^a$ are as defined above; and
R1, R3 and R4 are the same or different and each, independently, represents hydrogen or alkyl, wherein the alkyl group is optionally substituted by R$^b$;
E represents a group of formula i or vii

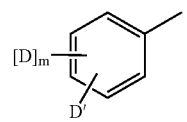

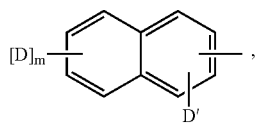

wherein
D represents H, alkyl, acyl, aryl, alkylaryl, halogen, —CN and NO$_2$, wherein the alkyl, aryl, or alkylaryl group is optionally substituted by R$^b$;
m is an integer 0 or 1; and
D' represents halogen;
D" represents hydrogen or alkyl; and
L represents (CH$_2$)$_a$Z$^1$(CH$_2$)$_b$Z$^2$ wherein a is 0, 1, 2 or 3; Z$^1$ is absent; b is 1, 2 or 3; and Z$^2$ is R'N—CO—NR$^t$ wherein is H, aryl, alkylcycloalkyl, alkylbiphenylyl wherein each alkyl chain may be substituted by one or more hydroxy or alkoxy.

2. The compound of claim 1 wherein A is situated in the para position (relative to group -L-E).

3. The compound of claim 1 wherein A represents

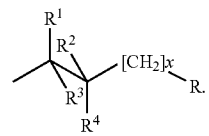

4. The compound of claim 1 wherein R$^1$, R$^3$ and R$^4$ are H.
5. The compound of claim 1 wherein R$^2$ is O-ethyl.
6. The compound of claim 1 wherein R is OH.
7. The compound of claim 1 wherein D" is H.
8. The compound of claim 1 wherein E is

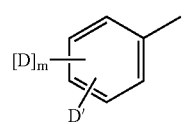

9. The compound of claim 8 wherein D and D" are fluoro.
10. The compound of claim 8 wherein m is 1.
11. The compound of claim 1 wherein L is (CH$_2$)$_a$Z$^1$(CH$_2$)$_b$Z2 wherein a is 0; Z$^1$ is absent; b is 2; and Z$^2$ is —N(alkyl)—CO—N(H)—.
12. The compound of claim 1 wherein A is situated in the para position (relative to group -L-E) and represents

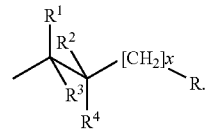

13. The compound of claim 1 wherein R$^1$ , R$^3$ , and R$^4$ are H; R$^2$ is O-ethyl; and R is OH.
14. The compound of claim 1 wherein D" is H and E is

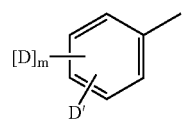

wherein D and D' are fluoro; and m is 1.
15. The compound of claim 1 wherein:
A is situated in the para position (relative to group -L-E) and represents

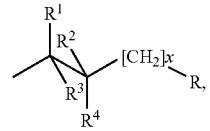

wherein
 $R^1$, $R^3$, and $R^4$ are H;
 $R^2$ is O-ethyl;
 R is OH;
D' is H;
E is
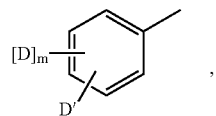,
wherein
 D and D' are fluoro;
 m is 1; and
L is $(CH_2)_a Z1 (CH_2)_b Z^2$ wherein
 a is 0;
 $Z^1$ is absent;
 b is 2; and $Z^2$ is —N(alkyl)—CO—N(H)—.
16. N'-(2,4-difluorophenyl)-N-(2-{4-[(2S)-2-ethoxy-3-hydroxypropyl]phenyl}ethyl)-N-heptylurea.
* * * * *